United States Patent [19]

Kieturakis

[11] Patent Number: 5,662,673
[45] Date of Patent: Sep. 2, 1997

[54] SURGICAL TROCAR AND METHOD FOR PLACING A TROCAR SLEEVE IN A BODY WALL

[76] Inventor: Maciej J. Kieturakis, 372 Beverly Dr., San Carlos, Calif. 94070

[21] Appl. No.: 417,009

[22] Filed: Apr. 5, 1995

[51] Int. Cl.⁶ .................................................. A61B 17/34
[52] U.S. Cl. ........................ 606/185; 604/264; 411/387
[58] Field of Search .................... 411/29, 387; 606/73, 606/185; 604/164, 264, 272

[56] References Cited

U.S. PATENT DOCUMENTS

| | | | |
|---|---|---|---|
| 936,379 | 10/1909 | Stevens . | |
| 3,096,962 | 7/1963 | Meijs . | |
| 4,191,191 | 3/1980 | Auburn | 606/185 |
| 4,535,773 | 8/1985 | Yoon | 604/169 |
| 4,601,710 | 7/1986 | Moll | 604/165 |
| 4,654,030 | 3/1987 | Moll et al. | 604/165 |
| 4,836,205 | 6/1989 | Barrett | 128/340 |
| 4,867,404 | 9/1989 | Harrington et al. | 248/231.4 |
| 4,881,537 | 11/1989 | Henning | 604/84 |
| 5,116,353 | 5/1992 | Green | 606/184 |
| 5,147,316 | 9/1992 | Castillenti | 604/164 |
| 5,147,376 | 9/1992 | Pianetti | 606/170 |
| 5,201,325 | 4/1993 | McEwen et al. | 428/779 |
| 5,203,773 | 4/1993 | Green | 606/104 |
| 5,209,736 | 5/1993 | Stephens et al. | 604/164 |
| 5,224,952 | 7/1993 | Deniega et al. | 604/164 |
| 5,226,890 | 7/1993 | Ianniruberto et al. | 604/164 |
| 5,232,451 | 8/1993 | Freitas et al. | 606/174 |
| 5,246,425 | 9/1993 | Hunsberger et al. | 604/272 |
| 5,258,003 | 11/1993 | Ciaglia et al. | 606/185 |
| 5,271,380 | 12/1993 | Riek et al. | 606/164 |
| 5,279,567 | 1/1994 | Ciaglia et al. | 604/117 |
| 5,284,130 | 2/1994 | Ratliff | 606/1 |
| 5,312,357 | 5/1994 | Buijs et al. | 604/164 |
| 5,334,185 | 8/1994 | Giesy et al. | 604/164 |
| 5,336,237 | 8/1994 | Chin et al. | 606/167 |
| 5,346,504 | 9/1994 | Ortiz et al. | 606/192 |
| 5,348,541 | 9/1994 | Lyell | 604/164 |
| 5,368,598 | 11/1994 | Hasson | 606/119 |
| 5,370,109 | 12/1994 | Cuny | 606/198 |
| 5,431,655 | 7/1995 | Melker et al. | 606/185 |

FOREIGN PATENT DOCUMENTS

| | | | |
|---|---|---|---|
| 149-431-A | 7/1985 | European Pat. Off. | 604/264 |
| 93/20866 | 10/1993 | WIPO | 604/264 |
| WO94/27513 | 12/1994 | WIPO | 604/164 |

Primary Examiner—Michael Buiz
Assistant Examiner—Patrick W. Rasche
Attorney, Agent, or Firm—Skjerven, Morrill, MacPherson, Franklin & Friel; Norman R. Klivans

[57] ABSTRACT

A safety incising instrument for helically incising a pathway through a body wall at a controlled rate without exerting longitudinal forces on the instrument. The instrument incorporates a helix assembly with a helically-protruding edge made of two cooperating elements: a tapered blade element with a sharp helical blade edge and a resilient shield element with a dull helical edge. The blade and shield elements mate along helical interfaces and jointly define the helically-protruding edge. A periphery of the helix is transformable between an incising position in which the sharp blade edge is exposed and a non-incising position in which the sharp blade edge is not exposed. The shield element is made of resilient material and tissue counterforce or drag on the shield causes the helix to transform to the incising position to incise a pathway in the body wall. Upon penetration of the body wall, the reduction in tissue counterforce on the resilient shield causes the helically-protruding edge to transform to a dull edge thus protecting organs within an anatomic cavity from contact with any sharp blade edge.

15 Claims, 13 Drawing Sheets

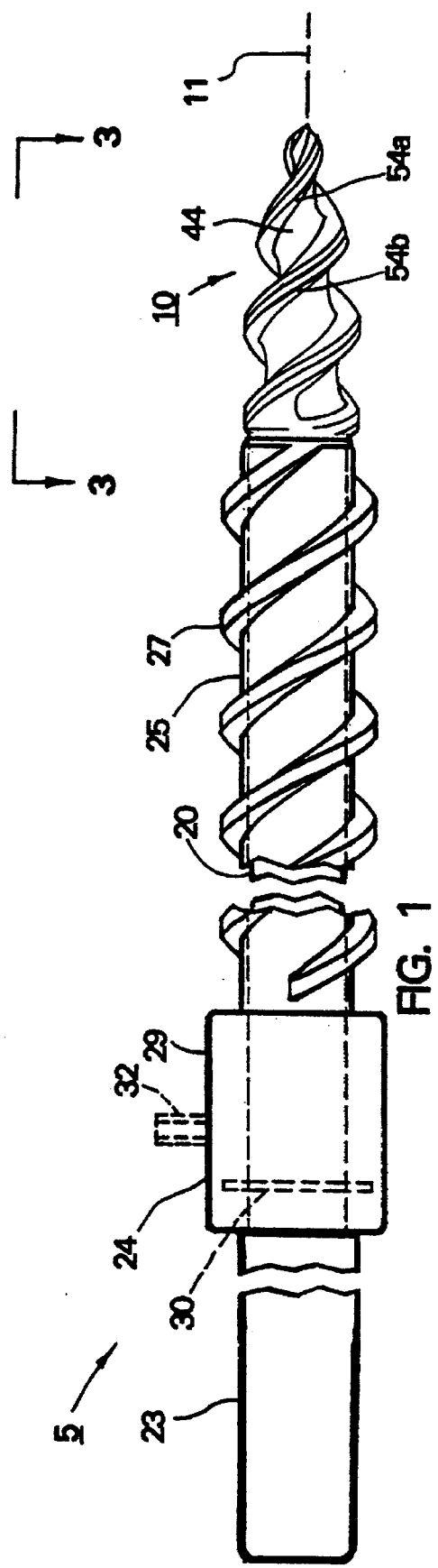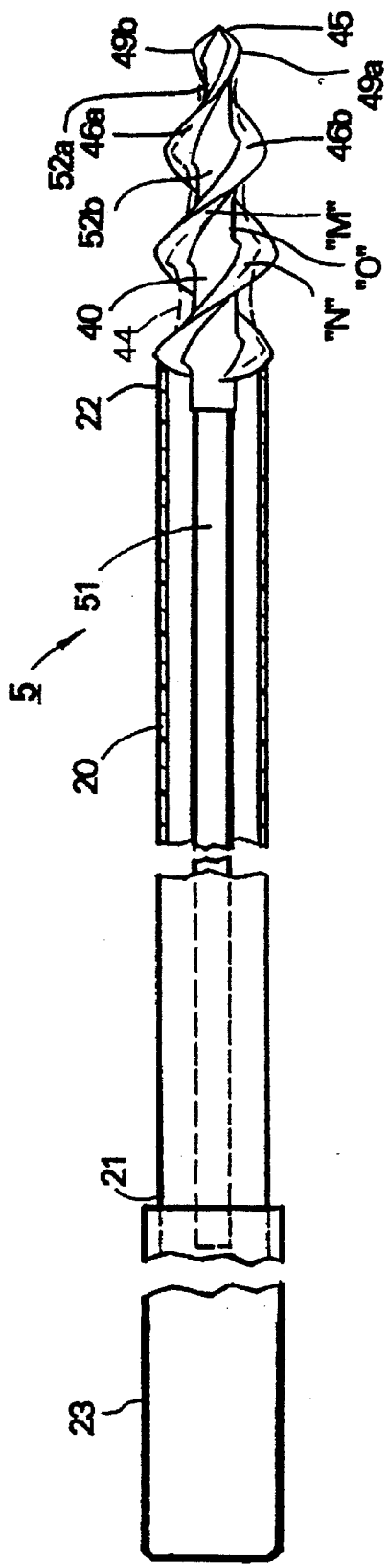

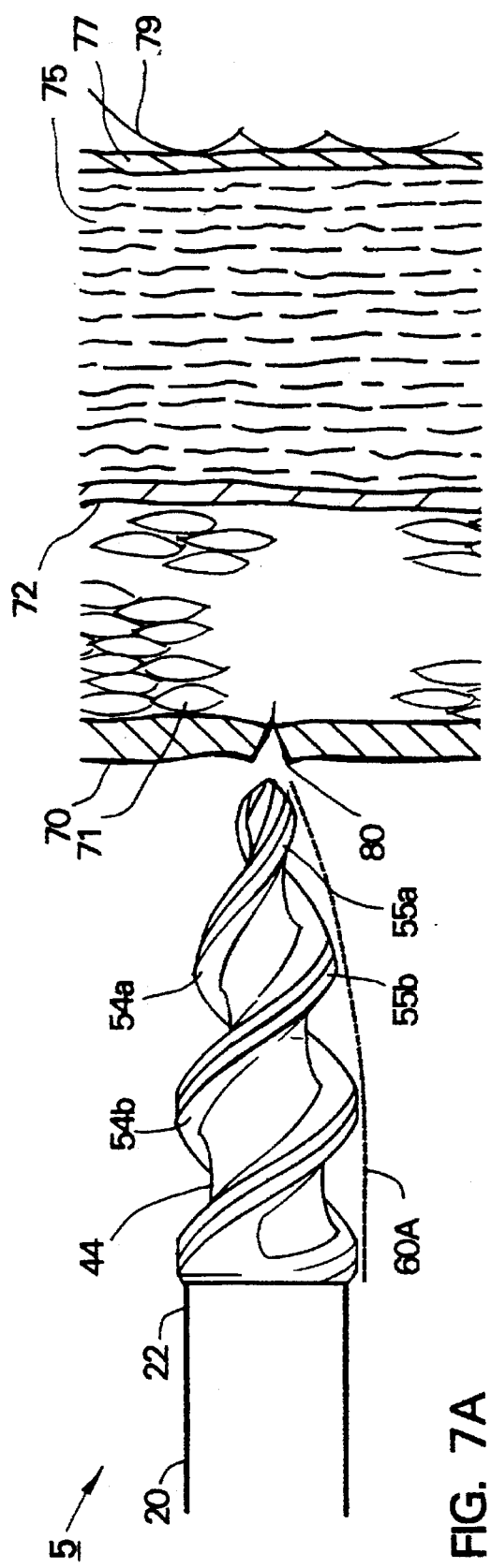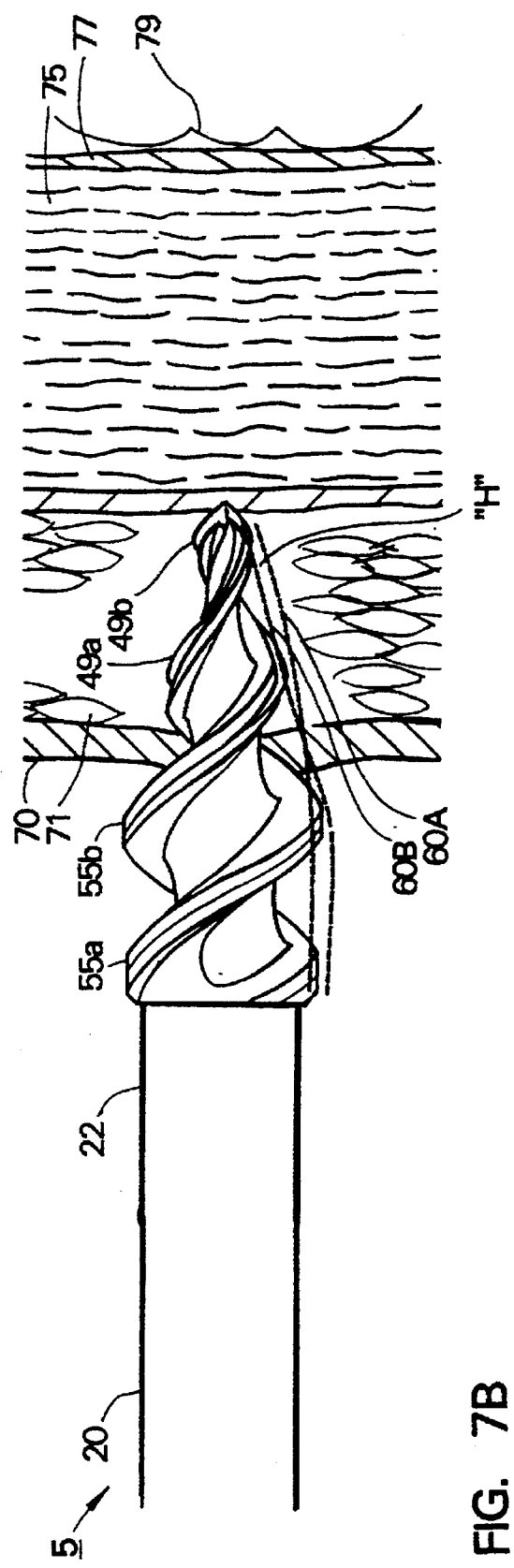
FIG. 7A
FIG. 7B

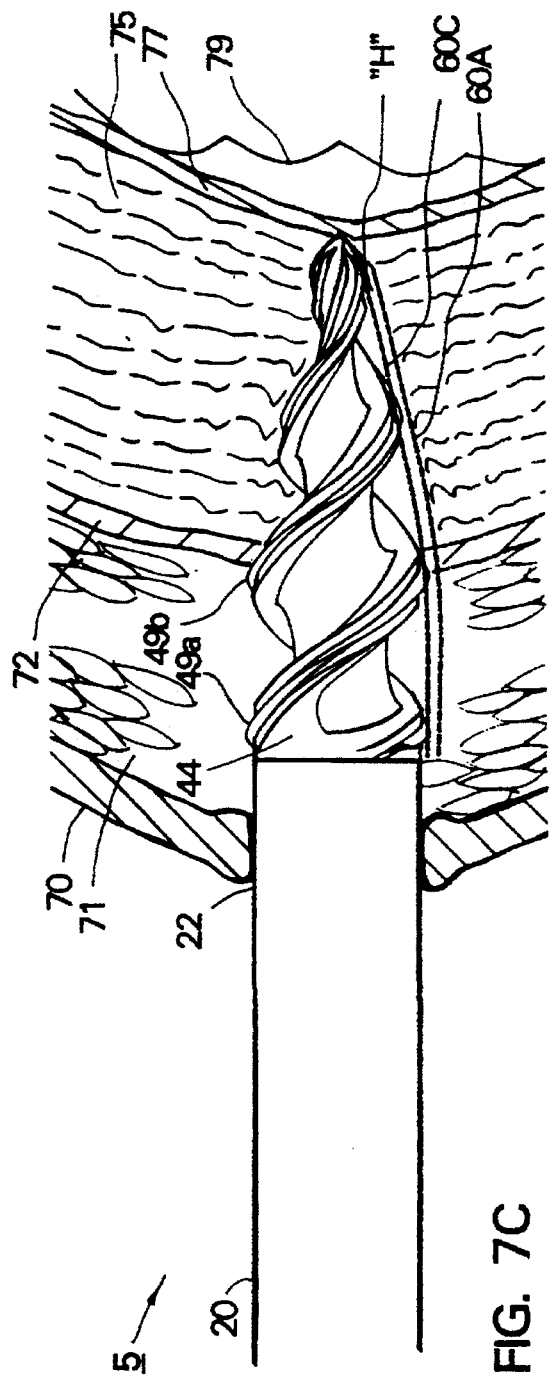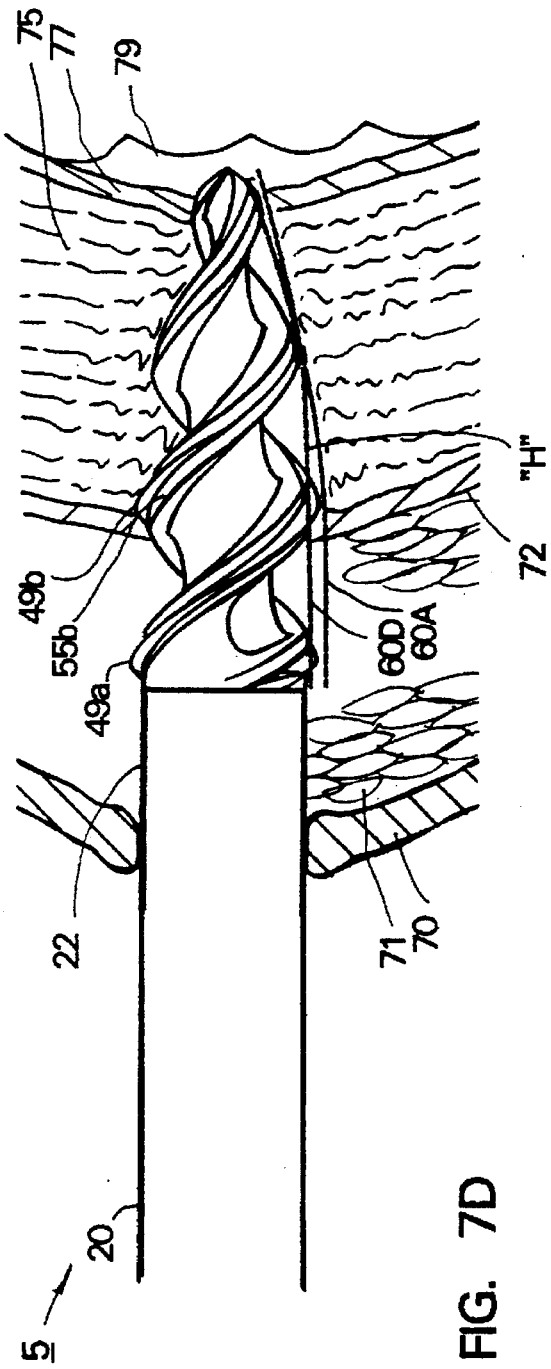

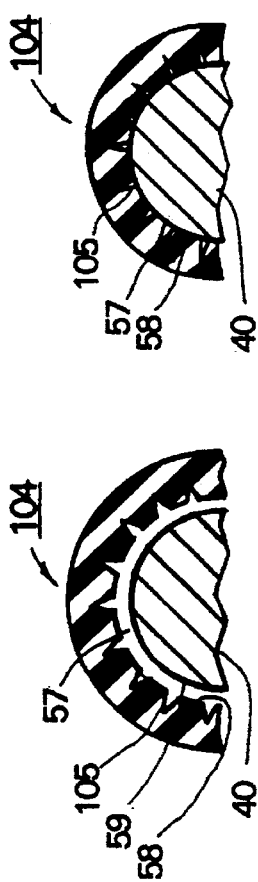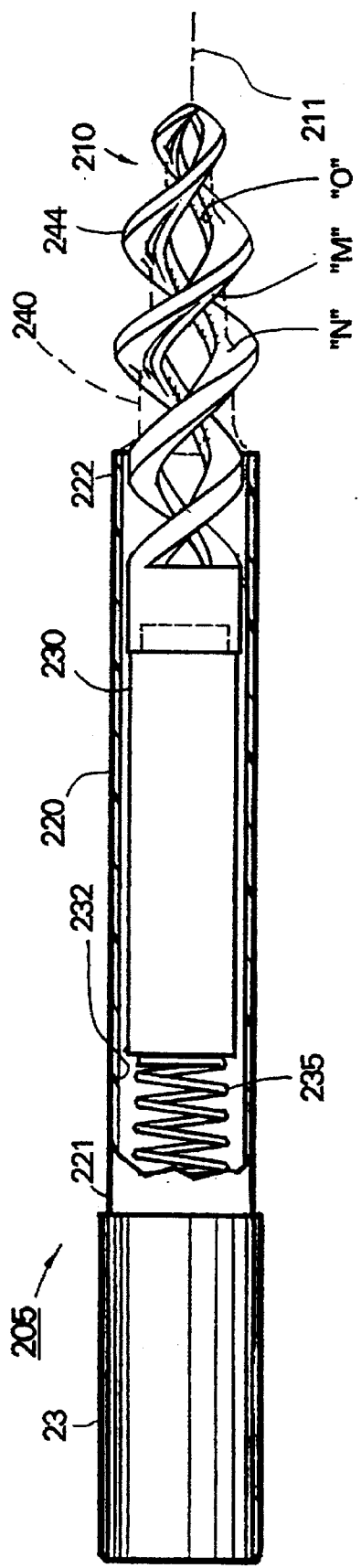
FIG. 8A
FIG. 8B
FIG. 9

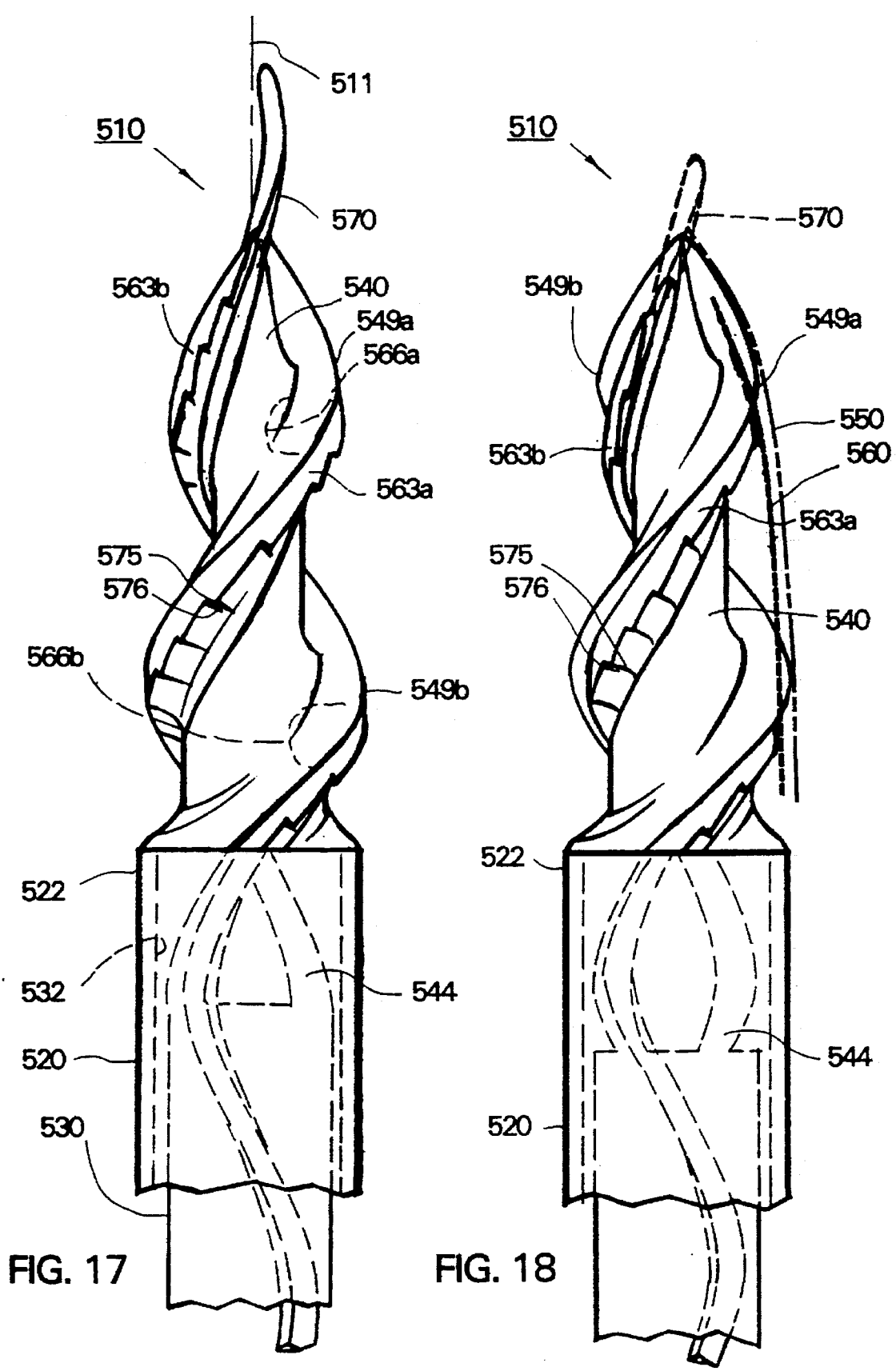

SURGICAL TROCAR AND METHOD FOR PLACING A TROCAR SLEEVE IN A BODY WALL

CROSS-REFERENCE TO RELATED APPLICATIONS

This application is related to and commonly invented U.S. patent application Ser. No. 08/316,164 filed Sept. 30, 1994 U.S. Pat. No. 5,591,191, issued on Jan. 7, 1997 which is a continuation-in-part of Ser. No. 08/187,753 filed Jan. 26, 1994 now abandoned.

BACKGROUND OF THE INVENTION

1. Field of the Invention

This invention relates to surgical instrumentation and more particularly to a trocar-type instrument and method for incising a pathway through tissue overlying an anatomic cavity and for placing a trocar sleeve or cannula within the incised pathway to provide access to the interior of the body.

2. Description of Prior Art

In abdominal "endoscopic" surgeries, a surgeon typically insufflates the abdominal cavity with $CO_2$ gas to separate the abdominal wall from viscera. A trocar then is used to puncture a pathway through tissue overlying the abdominal cavity and to place a trocar sleeve in the abdominal wall. A trocar is a shafted instrument typically configured with a three-faced pyramidal piercing tip from which the name trocar is derived: trois (three) and carre' (sides or faces). Trocars suffer from the disadvantage of requiring powerful thrusting forces to puncture a path through tissue. The sharp tip and edges of the trocar can cause injury to an internal organ upon the slightest contact.

Commercially available safety trocars typically use a spring-loaded protective shield that springs forward to cover the sharp tip after the tip enters the abdominal cavity. Attempts to shield trocar tips within axially-reciprocating shields after penetration into an anatomic cavity are undesirable because the trocar tip must pierce fully into the cavity before the shield is triggered. Such trocars also rely on insufflation to prevent a trocar tip from lacerating internal organs. Insufflation is undesirable because it is time-consuming. There is therefore a need for new instruments and methods for safely incising a path through body wall with or without insufflation.

SUMMARY OF THE INVENTION

The present invention relates to a helical incising instrument that allows a surgeon to incise a pathway through a body wall at a controlled rate without exerting longitudinal forces on the instrument. Since the term "trocar" now is widely used to describe instruments for placing a sleeve in a body wall, this disclosure will adopt the term "trocar" or "helical trocar" to describe the present invention, although the instrument disclosed does not have a three-faced pyramidal tip from which the term "trocar" is derived.

The helical trocar has an incising assembly with a helically protruding edge for threadably engaging tissue. The helical edge is capable of transformation between dull and sharp, or from a "non-incising" position to an "incising" position. The transformation of the helical edge is responsive to tissue counterforces acting on the incising assembly. As the incising assembly is helically advanced into tissue, the helical edge remains sharp. After the incising assembly penetrates the body wall, the reduction of tissue counterforce causes the helical edge to be transformed to the dull position to protect organs within the abdominal cavity from contact with a sharp helical edge.

The helical trocar has a helix that is formed of two mating components: a first (blade) element with a sharp helical edge portion and a second (shield) element with a dull helical edge. The first and second elements mate along helical interfaces and jointly define the helical edge. Both the first and second elements have tapered peripheries (blade periphery and shield periphery) that are in registration in the "non-incising" position so that the sharp blade edges are not exposed outside the shield. The shield is made of a resilient plastic material. Tissue counterforce on the shield will deform the shield radially inward to expose the helical blade edge.

In an exemplary method, assume the surgeon wishes to incise a pathway into the abdominal cavity and place a trocar sleeve within the pathway. The surgeon grasps the instrument handle and presses the tip of the instrument into a nick in the patient's skin. As the instrument is helically advanced into tissue, the shield is deformed radially inward to slightly expose the blade periphery outwardly from the shield periphery to provide the "incising" position. Thus, a razor-sharp helical blade edge is exposed as the surgeon continues to advance the instrument inwardly. While advancing the instrument, the helical edge threadably engages tissue as a screw, and the surgeon may lift the body wall proximally away from internal organs. As the distalmost blade edge incises the peritoneum, tissue counterforce is relaxed against the distal portion of the resilient shield causing that portion of the shield to rebound or expand radially outward to the non-incising position to prevent any sharp blade edge from contacting internal organs.

With the distal portion of the helix in the nonincising position, the helical periphery of the helix still engages tissue of the abdominal wall. The surgeon continues to rotate the instrument thus dilating the pathway to accommodate the instrument. The trocar sleeve also may be continuously threaded to threadably engage tissue. After the helix is advanced into the abdominal cavity, the trocar may be withdrawn from the trocar sleeve leaving the sleeve in place within the abdominal wall.

Other embodiments of incising helixes have a shield element that may travel helically relative to the blade element, together with radial inward compression of the shield to expose the helical blade edge. Still another embodiment of incising helix has a rigid shield element that only travels helically relative to the blade element to expose the helical blade edge. Still another embodiment of incising helix has a helical probe member that is adapted to project distally upon penetration of a body wall. Still another embodiment of incising helix is of transparent material to allow endoscopic viewing therethrough.

In general, the present invention advantageously provides an incising instrument and method for helically incising a pathway through tissue that does not require the application of thrusting longitudinal forces as with puncturing trocars. The present invention also provides an instrument and method that applies forces that are only tangential to the axis of travel. The present invention provides an instrument and method that utilizes a helical blade to allow a slow and controlled rate of advancement through tissue.

The present invention advantageously provides an instrument and method that allows a surgeon to incise a pathway through an anatomic wall without a sharp blade entering into the anatomic cavity as a means of preventing inadvertent contact with internal organs. The present invention also provides an instrument and method that allows the surgeon to apply proximal traction to the body wall to lift the body wall away from internal organs as the instrument penetrates the body wall.

The present invention advantageously provides an instrument and method that makes only shallow helical incisions in tissue that allow for rapid healing of blood vessels.

The present invention advantageously provides an instrument that has a resilient helical shield for resiliently shielding a helical blade edge. The present invention provides a resilient helical that is deformable by tissue counterforce to expose a sharp blade edge.

The present invention advantageously provides an instrument that has a resilient helical shield that is capable of helical travel for shielding a helical blade edge. The present invention provides a helically traveling shield that is spring-loaded to travel helically to shield the blade edge.

The present invention advantageously provides an instrument that has helical probe that is spring-loaded to project distally upon penetration of a body wall to push internal organs away from the distal end of the instrument.

The present invention also provides an incising assembly of transparent material to allow endoscopic viewing therethrough.

Additional advantages and features of the invention appear in the following description in which several embodiments are set forth in conjunction with the accompanying drawings.

BRIEF DESCRIPTION OF THE DRAWINGS

FIG. 1 is an elevational view of a helical trocar and cannula assembly of the present invention.

FIG. 2 is a partial sectional of the helical trocar of FIG. 1 showing first or blade element of the helix subassembly of FIG. 1.

FIGS. 7A–7F are a sequence of cut-away views showing the manner in which the helix subassembly of FIGS. 3–6 is utilized to perform a method of the present invention.

FIGS. 8A–8B are transverse sectional views of an alternative embodiment of a shield element of a helix subassembly.

FIG. 9 is a partial sectional view of an alternative embodiment of helical trocar.

FIG. 17 is an elevational view of a helix subassembly of an alternative embodiment of helical trocar in a non-incising position.

FIG. 18 is an elevational view of the helix subassembly of FIG. 17 in an incising position.

DESCRIPTION OF PREFERRED EMBODIMENTS OF THE INVENTION

Figures 3, 4:
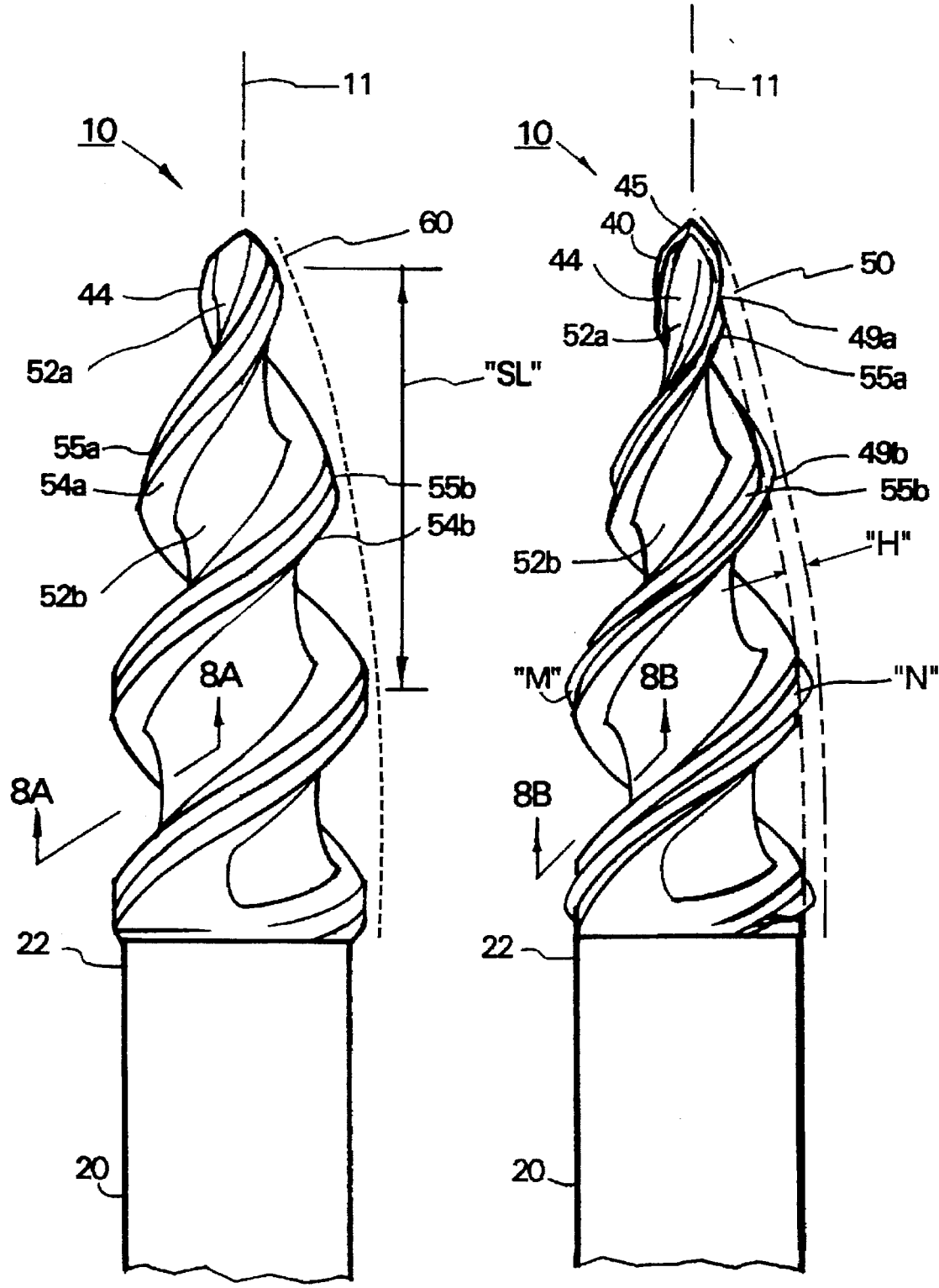
FIG. 3 is an elevational view of a the helix subassembly of FIG. 1 taken along line 3—3 of FIG. 1 illustrating a non-incising position.
FIG. 4 is an elevational view of the helix subassembly of FIG. 3 illustrating an incising position.

By way of example, FIGS. 1–2 depict helical trocar 5 with helix assembly 10 that is suitable for incising a pathway through a patient's abdominal wall or other body wall. More in particular, trocar 5 generally is cylindrical in shape extending along axis 11. Introducer sleeve 20 having proximal and distal ends, 21 and 22, includes handle portion 23 adapted for gripping by a human hand. Introducer sleeve 20, described further below, is dimensioned to cooperate with a cannula assembly 24 and cannula 25 and is shown in the accompanying drawings in 10 mm. diameter. Such cannulas may range in diameter from 5 mm. to 25 mm. or more (not limiting). Cannula 25 incorporates continuous helical threads 27 that correspond to the helical form of helix subassembly 10. Cannula body 29 is of any suitable shape and dimension to accommodate a conventional valve 30 and insufflation port 32 (see FIG. 1).

Referring to FIGS. 1–2, helix subassembly 10 is coupled to distal end 22 of introducer sleeve 20. As shown in FIGS. 3–6, helix subassembly 10 comprises two helically-mating components, first element 40 (alternatively "blade") and second element 44 (alternatively "shield"). Blade and shield, 40 and 44 interfit and slidably mate along helical interfaces, "M", "N" and "O", which correspond to helical surfaces of blade element 40. In FIGS. 3–6, such helical surfaces, "M", "W", and "O", between blade 40 and shield 44 are generated by constant spiral lead "SL" of approximately 1.00", but such spiral lead may range from less than 0.20" to 3.00" or more and be within the scope of the present invention. Spiral lead "SL" generally is equal to the axial travel of variform helix 10 in tissue through 360° rotation.

In FIGS. 3–6, helix subassembly 10 has a double-lead configuration of helical protrusions or threads, but it should be appreciated that a helix subassembly may have a single-lead or plural-lead and fall within the scope of the present invention.

More specifically referring to FIG. 2, shield 44 is shown in phantom view to reveal blade 40 with a screw-type form having distal tip 45. Double-lead blade protrusions 46a and 46b in blade 40 have edges, 49a and 49b, that are sharp and capable of incising tissue. Blade edges 49a and 49b are circumscribed by blade periphery 50. Blade periphery 50 of blade 40 exhibits a decreasing transverse cross-section or taper in the distal direction. Blade periphery 50 may be any done-shape, bullet-shape or ball-end shape and fall within the scope of the present invention. Bladder 40 may be of metal and fabricated by grinding, casting, milling, forming, thread rolling or any other suitable manufacturing process. Blade 40 also may be made of a plastic capable of having a relatively sharp edge (e.g., Delrin®) or a plastic with a metal edge-insert or a metal tip-insert. The proximal portion of blade 40 is coupled to metal or plastic shaft 51 by any suitable means such as adhesives or a press fit. Shaft 51 and sleeve 20 are fixedly coupled together at either a proximal or distal portion of trocar 5, and are depicted in FIG. 2 coupled together at handle portion 23.

Referring now to FIGS. 3 and. 5, shield element 44 is depicted mated with blade element 40 showing the resilient shield in a non-incising ("repose") position. Shield 44 is molded of a semi-soft, semi-rigid or flexible resilient material (e.g., Polyurethane, Silicon, Silastic®, Nylon®) and is dimensioned to fit in helical channels 52a and 52b that lie between blade protrusions 46a and 46b of blade 40. The outer radial edge of shield protrusions 54a and 54b have lands 55a and 55b that are flat, rounded or generally dull. As can be seen in FIG. 3, lands 55a and 55b are split such that the blade edges of blade 40 are covered by the outer edge of shield protrusions 54a and 54b.

Figures 5, 6:
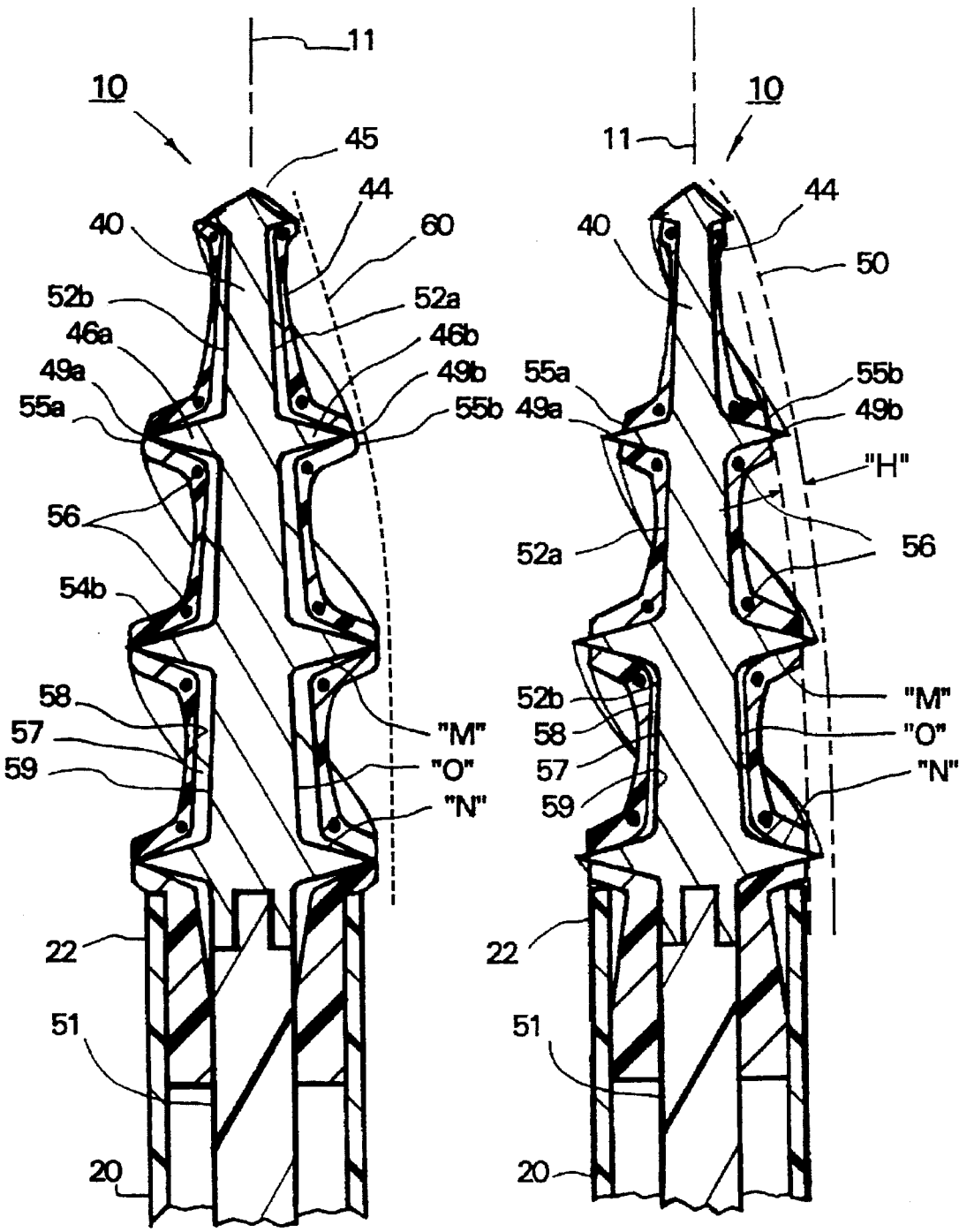
FIG. 5 is a sectional view of the helix subassembly of FIG. 3 taken along line 5—5 of FIG. 3.
FIG. 6 is a sectional view of the helix subassembly of FIG. 4 taken along line 6—6 of FIG. 4.

As described above, shield 44 may be made of relatively soft material, and could tend to unwrap from blade 40. To prevent such unwrapping, FIGS. 5–6 show deformable coil springs 56 (or coils, collectively) of spring steel molded into shield 44 that help to maintain the shield in its repose state of FIGS. 3 and 5. If shield 44 is of more rigid material such as Nylon®, such coil springs may not be required. As can be seen in FIGS. 3 and 5, in the repose (non-incising) position, gap 57 exists between inner surface 58 of shield 44 and outer surface 59 of blade 40 (along interface "O").

The outer periphery of shield 44 (lands 55a and 55b) is circumscribed by shield envelope or periphery 60. Shield periphery 60 of shield 44 exhibits a decreasing transverse cross-section or taper that corresponds in shape to blade periphery 50.

Referring to FIGS. 4 and 6, it now can be seen that blade element 40 and shield element 44 may be transformed to an incising (or "suspense") position in which edges 49a and 49b (or blade periphery 50) are exposed outside shield periphery 60. The transformation of helix 10 to the incising or suspense position from the non-incising or repose position is caused by a counterforce that deforms the flexible material of shield 44, as further described below.

To make helix 10 capable of incising a pathway, blade edges 49a and 49b need only be exposed slightly (blade exposure "H") beyond lands 55a and 55b, for example as little as from 0.010" to 0.030", to accomplish the objective of incising tissue. The accompanying drawings illustrate a somewhat exaggerated blade exposure "H" for purposes of clarity, and "H" dimensions ranging from 0.010" to 0.150" are not limiting for various diameter helixes.

FIGS. 7A–7F now briefly illustrate the manner in which instrument 5 and helix subassembly 10 is utilized to perform the method of the present invention in incising a pathway through a patient's abdominal wall, including skin 70, fat layer 71, fascia 72, muscles 75 and peritoneum 77. Internal organs 79 are depicted within the abdominal cavity.

Referring to FIG. 7A, instrument 5 is depicted in the non-incising (repose) position and is gripped by a human hand (not shown) preparatory to helically incising a pathway in the abdominal wall. The outer envelope of shield 44 is depicted by repose periphery 60A.

As can be seen in FIG. 7B, the surgeon presses the distal end of the instrument into nick 80 in skin 70 and then rotates instrument 5 clockwise causing helical counterforce or tissue drag against the distal portion of shield 44. Such counterforce causes the distal portion of shield 44 to be compressed radially inward and counter-rotated slightly (helically and proximally) due to the resilient nature of the material of shield 44. Thus, tissue counterforce upon helical and distal advancement of helix 10 causes the subassembly to transform partly to the incising (suspense) position from the non-incising (repose) position. Note in FIG. 7B, the proximal portion of shield 44 has not been compressed by tissue counterforce, thus leaving the proximal blade edge covered by the shield. In fact, the proximal portion of shield 44 may be expanded radially outward by the helical counter-rotation of the shield, depending on the elasticity of shield 44. Thus, in FIG. 7B, the shield's periphery is depicted as suspense periphery 60B, and may be compared with the shield's repose periphery 60A.

FIG. 7C illustrates helix 10 as the surgeon further advances the instrument through fat 71, fascia 72, and muscles 75. It can be seen in FIG. 7C that tissue counterforce on resilient shield 44 caused all of blade edges 49a and 49b to be exposed outside lands 55a and 55b. The shield's suspense periphery 60C may be compared to repose periphery 60A. FIG. 7C further depicts tip 45 of blade edges 49a and 49b beginning to incise peritoneum 77.

FIG. 7C illustrates that the surgeon may exert proximal traction on trocar 5 during its helical advancement to lift the abdominal wall. It should be appreciated that the radial depth "D" of channels 52a and 52b as well as the angle of proximal faces of shield protrusions 54a and 54b are configured to adequately grip tissue (see FIGS. 3–4). With the helix threadably anchored in tissue, such proximal traction allows the surgeon to lift the wall away from internal organs as a safety precaution, which is to be contrasted with puncturing trocars in which axial forces are necessary to puncture inwardly thus pushing the abdominal wall inwardly into internal organs.

FIG. 7D follows an instant after FIG. 7C when the distal tip of helix 10 penetrates peritoneum 77. Upon penetration of peritoneum 77, the relaxation of tissue counterforce against the distal end of shield 44 causes the distal portion of the shield to expand radially outward under the resilient spring force of the material of shield 44 together with the spring force of coil springs 56 (collectively). Thus, penetration of the abdominal wall causes the distal portion of helix 10 to transform to a non-incising (repose) position to prevent any sharp blade edge from contacting internal organs 79 in the abdominal cavity.

Of particular interest to the present invention, referring to FIG. 7D, the radial inward forces and proximal counterforces on the distal portion of shield 44 also helically loads (winds up) the spring structure of the resilient shield and coil springs 56. In other words, the shield moves slightly helically in channels 52a and 52b caused by tissue counterforce. Hence, upon penetration of the abdominal wall, the distal portion of shield 44 also will move helically and distally slightly (along with its distalmost radial expansion) to cover the distal blade edges. The shield's suspense periphery 60D upon penetration of the peritoneum may be compared with repose periphery 60A.

Figure 7E:
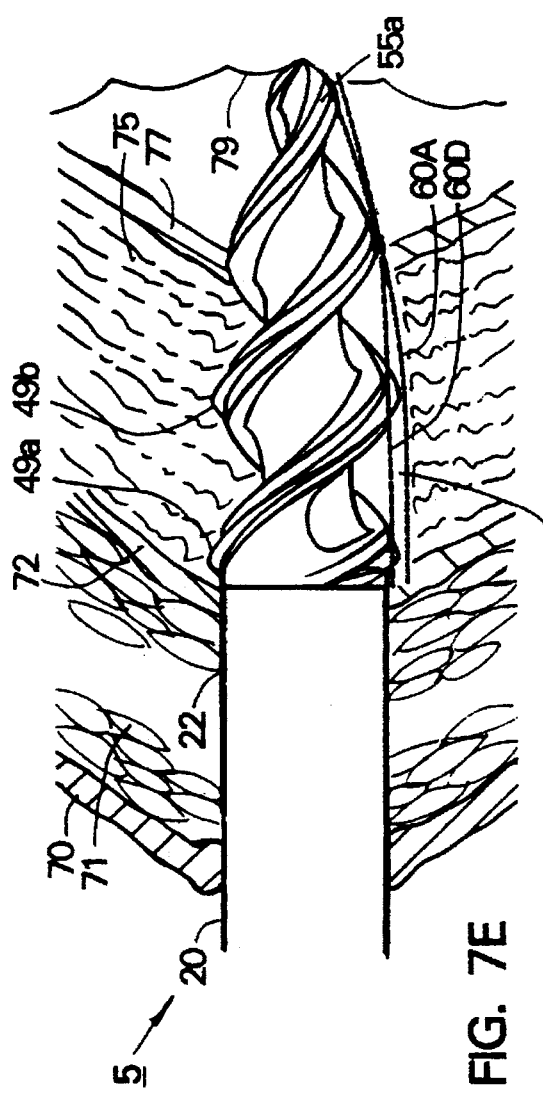

Also of particular interest to the present invention, referring to FIG. 7E, the transverse dimension of the incised pathway is dilated to accommodate the diameter of sleeve 20 by the increasing transverse dimension (in the proximal direction) of helical channels 52a and 52b. As can also be seen in FIG. 7E, the slow rate of advancement of helix 10 into the abdominal cavity pushes the pliable internal organs 79 away from helix 10. Internal organs cause insufficient counterforce against shield 44 to cause the helix to transform to the incising (suspense) position. While advancing the instrument, proximal traction is still applied. The shield's suspense periphery 60D still exposes the proximal blade edges to incise the pathway slightly.

Figure 7F:
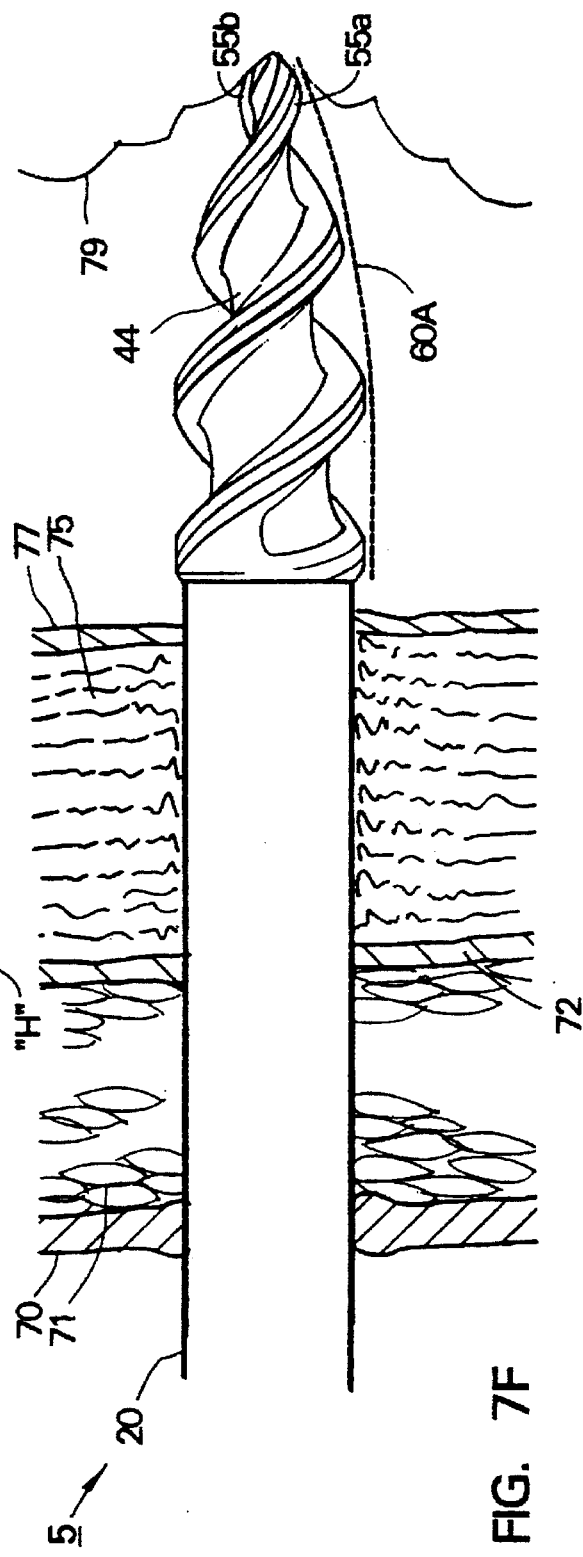

Referring to FIG. 7F, the surgeon helically advances helix 10 into the abdominal cavity. The helical protrusions 54a and 54b (FIG. 3) of helix 10 threadably engage tissue to drive the instrument inwardly (together with helical threads 27 of trocar sleeve 25 as shown in FIG. 1). As shown in FIG. 7F, the shield's periphery returns to its repose periphery 60A upon the relaxation of tissue counterforce. Trocar 5, if utilized with a trocar sleeve (not shown) then may be withdrawn from the incised pathway to provide access to the interior of the body.

It should be appreciated that blade exposure "H" (see FIGS. 4 and 6) in the distal portion of the helix may be less than blade exposure "H" in the proximal portion of the helix. For example, in the non-incising position, blade periphery 50 still may be exposed slightly outside shield periphery 60 and provide a safe means of incising a pathway in a body wall. Thus, the proximal portion of the helix may incise tissue at the same time the distal portion is dull and pushes internal organs away from the distal end of the helix.

FIGS. 8A–8B illustrate transverse sectional views of an alternative embodiment of shield 104, which is similar to a section of shield 44 taken along lines 8A—8A and 8B—8B of FIGS. 3 and 4. Like reference numbers refer to like elements of the above-described embodiment. FIGS. 8A–8B depict repose and suspense positions of shield 104 that is adapted to cooperate with blade 40, and its exterior surface 59. Shield 104 includes longitudinal compressing grooves 105 along its inner surface 58 to facilitate its inward compression by tissue counterforce from the repose position (FIG. 8A) to the suspense position (FIG. 8B). Grooves 105 are formed into shield 104 as part of molding shield 104 from resilient material. The provision of compression grooves allows shield 104 to be compressed radially inward to reduce gap 57 and to expose blade edges 49a and 49b without helically movement or distortion of shield 104 within helical channels 52a and 52b (cf. FIGS. 5–6).

Now turning to FIG. 9, another embodiment of helical trocar 205 is shown with helix assembly 210 having axis 211 that is suitable for incising a body wall. Trocar 205 differs from the above-described embodiment principally in that the shield element is adapted for greater helical travel (i.e., simultaneous axial and rotational travel) relative to the blade element in response to tissue counterforce or tissue drag, while at the same time the shield is of resilient material allowing for radial inward deformation between repose and suspense positions in response to tissue counterforce.

Introducer sleeve 220 (FIG. 9) having proximal and distal ends, 221 and 222, is dimensioned to slide within a standard-sized cannula or trocar sleeve. Inner sleeve 230 is slidably disposed in axial bore 232 of outer sleeve 220. Inner sleeve 230 is urged in the distal direction by spring 235. Spring 235 is a compression spring or a combination compression and torsion spring that imparts helical and distal movement to inner sleeve 230. As can be seen in FIG. 9 in phantom view, blade element 240 is fixed to distal end 222 of sleeve 220. Shield 244 is fixed to inner sleeve 230 by any suitable means such as adhesives.

Figure 10:
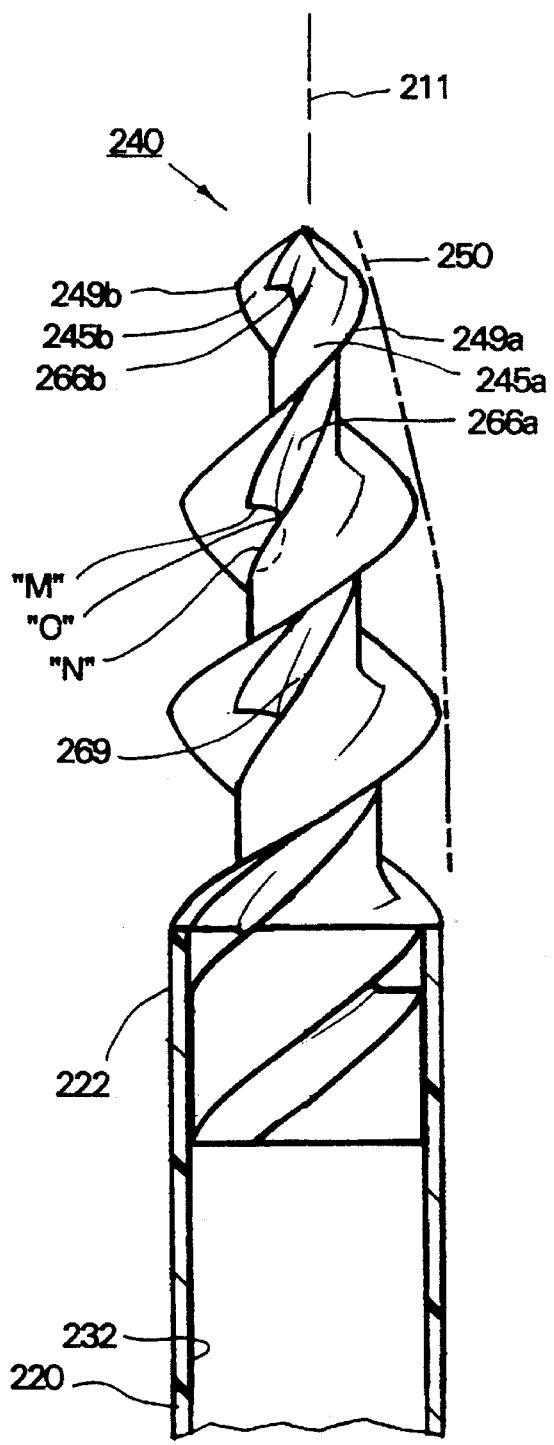
FIG. 10 is an enlarged elevational view of a de-mated first element or blade element of the alternative embodiment of trocar of FIG. 9.
Figure 11:
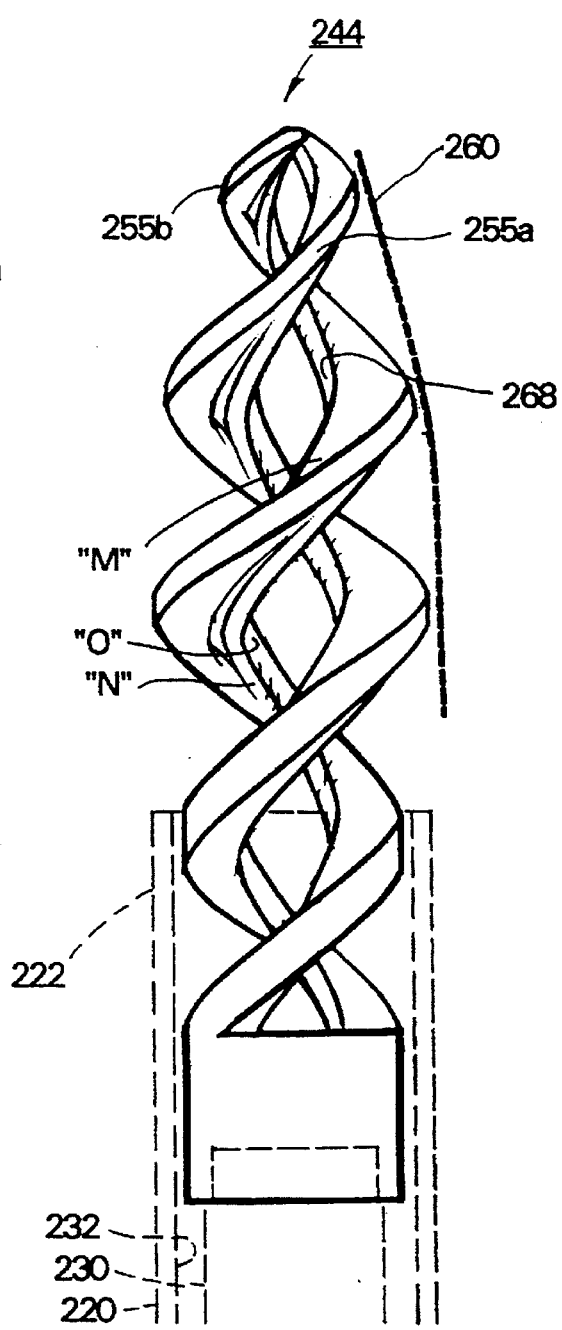
FIG. 11 is an elevational view of a de-mated second element or shield element that cooperates with the blade element of FIG. 9.

Referring to FIGS. 9–11, helix subassembly 210 is similar to the above-described embodiment and comprises two helically-mating components, first element 240 ("blade") and second element 244 ("shield"). Blade and shield, 240 and 244, interfit and slidably mate along helicoidal interfaces, "M", "N" and "O".

More specifically referring to FIG. 10, blade element 240 is shown de-mated. The double-lead helical protrusions, 245a and 245b, have helical blade edges, 249a and 249b, that are sharp. Blade edges 249a and 249b are circumscribed by blade periphery 250, which exhibits a decreasing transverse cross-section or taper toward the distal direction.

Now referring to FIG. 11, shield element 244 is shown de-mated from blade 240. The outer radial edge of shield 240 exhibit lands 255a and 255a that are flat, rounded or generally not sharp. The outer envelope of lands 255a and 255b is circumscribed by shield periphery 260. Shield periphery 260 of shield 244 exhibits a decreasing transverse cross-section which corresponds to blade periphery 250.

Figure 12:
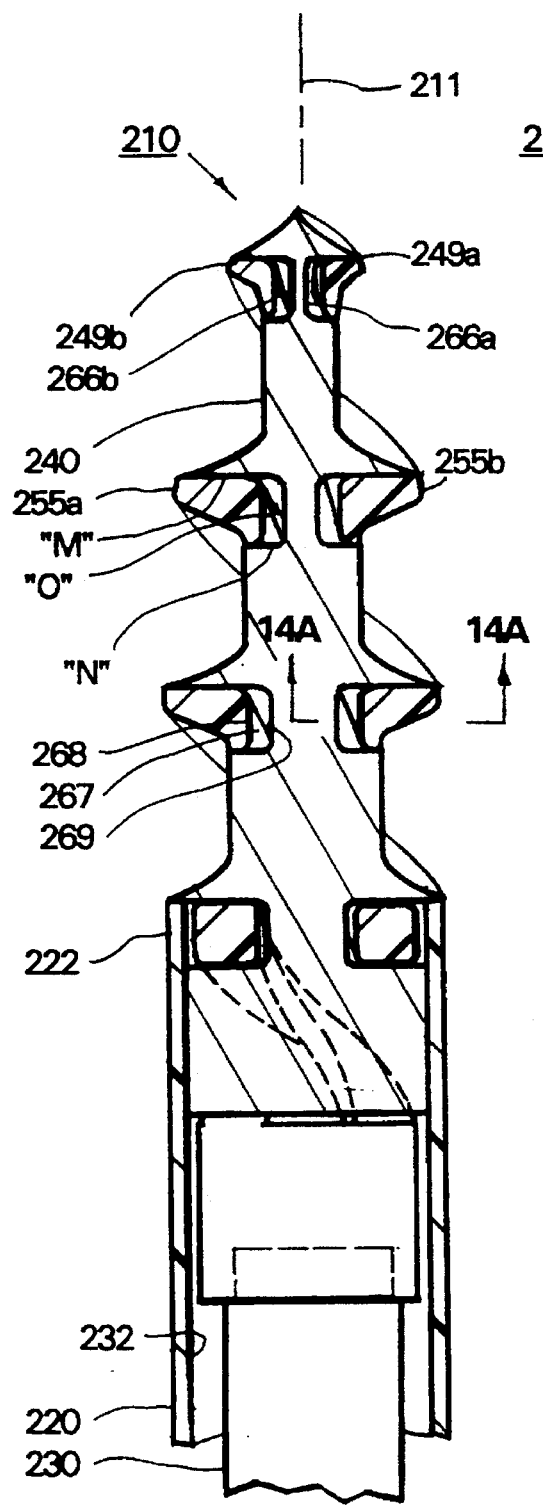
FIG. 12 is a sectional view of the helix subassembly of FIG. 9 taken along line 12—12 of FIG. 9 illustrating a non-incising position.
Figure 13:
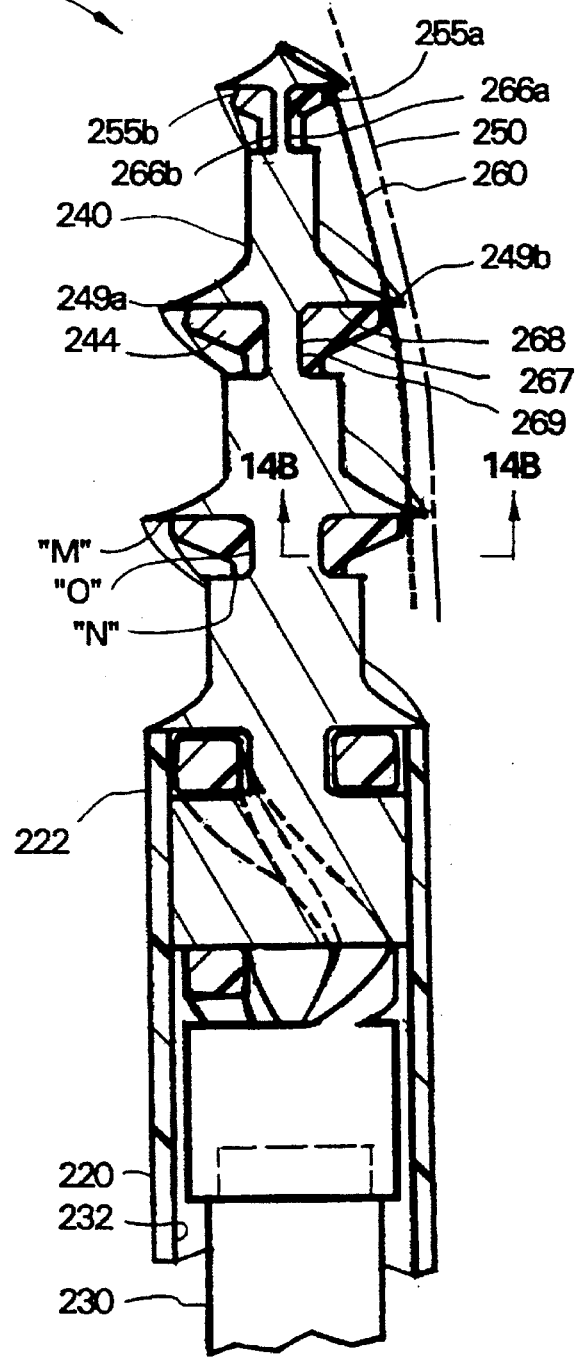
FIG. 13 is a sectional view of the helix subassembly of FIG. 12, but illustrating an incising position.

Referring to FIGS. 12–13, shield element 244 is depicted mated together with blade element 240 to illustrates the non-incising position (FIG. 12) and the incising position (FIG. 13). Shield 244 is molded of any suitable semi-rigid resilient plastic or other material (e.g., Delrin®) and is dimensioned to fit in helical channels 266a and 266b of blade 240. As can be seen in FIG. 12, lands 255a and 255b in the repose position cover the outer edges 249a and 249b of blade 240. FIG. 12 further shows, in the shield's repose position, gap 267 exists between an inner surface 268 of shield 244 and an outer surface 269 of blade 240 (non-incising position).

Now referring to FIG. 13, it can be seen that blade element 240 and shield element 244 may be transformed to an incising position in which blade edges 249a and 249b (blade periphery 250) is exposed outside shield periphery 260. The transformation of helix 210 to the incising position is caused by tissue counterforce or tissue drag on shield 244 that results in two effects: (i) the counterforce deforms the resilient material of shield 244 radially inwardly, and (ii) the counterforce overcomes the force exerted by spring 235 which causes shield 244 to travel helically and proximally in helical channels 266a and 266b. FIG. 13 shows gap 267 between inner surface 268 of shield 244 and outer surface 269 of blade 240 being reduced to zero. Also FIG. 13 shows shield element 244 counter-rotated helically relative to blade element 240 which overcomes the strength of spring 235, thus making helix subassembly 210 transform to the incising position (FIG. 13) from the non-incising position (FIG. 12).

The manner of utilizing helical trocar 205 to perform the method of the present invention in incising a pathway through a patient's body wall generally corresponds to the previously described FIGS. 7A through 7F. As the surgeon presses the distal end of instrument 205 into the body wall and rotates the instrument clockwise, tissue counterforce or tissue drag on shield 244 causes shield periphery 260 to be compressed radially inward and well as causing the shield to be counter-rotated (helically and proximally) overcoming the force of spring 235. Upon penetration of the body wall, the relaxation of counterforce or tissue drag on the distal end of shield 244 causes the shield to move helically and distally under the force exerted by spring 235 thus preventing any sharp blade edge from entering into the abdominal cavity.

Figure 14B:
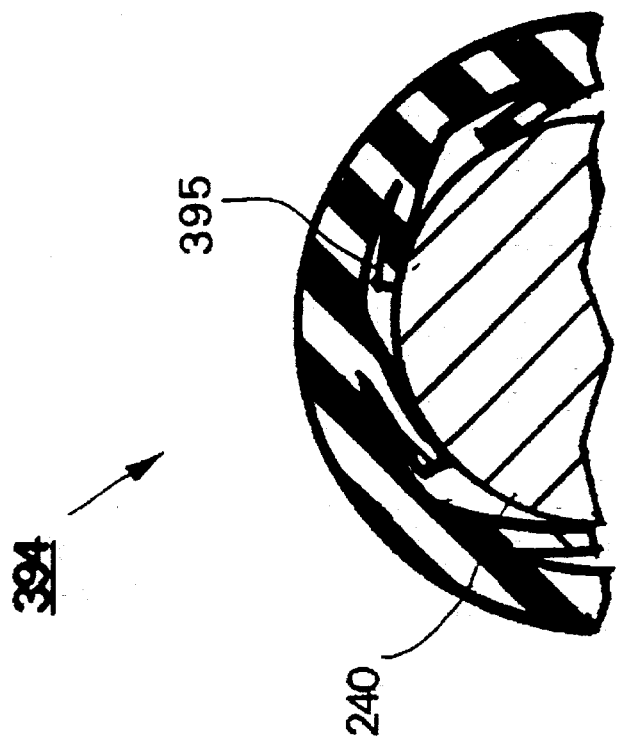
FIGS. 14A–14B are transverse sectional views of an alternative embodiment of a shield element of a helix subassembly.
Figure 14A:
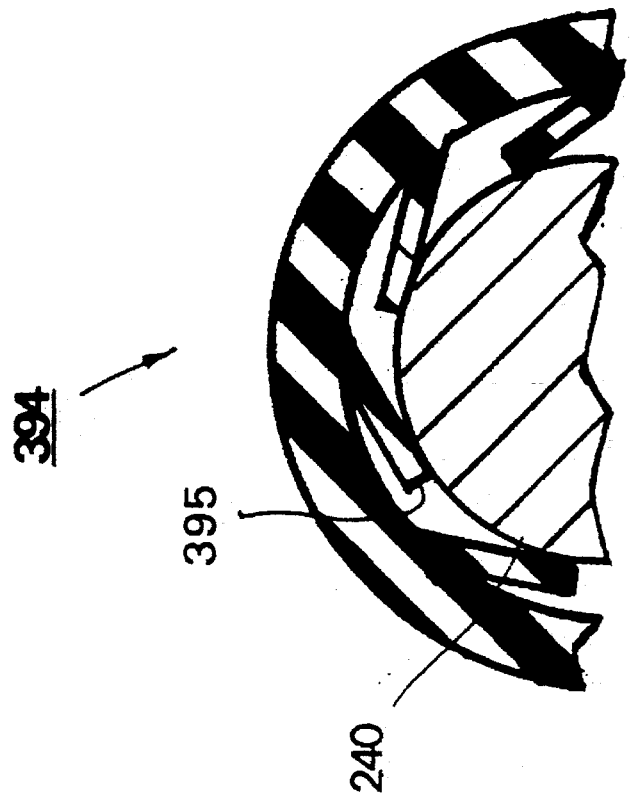

FIG. 14A–14B illustrate transverse sectional views of an alternative embodiment of a shield and is shown being similar to a section of shield 244 of FIG. 11. Alternative shield 394 of FIGS. 14A–14B is adapted to cooperate with above-described blade element 240. Shield 394 includes resilient spring arms 395 molded along inner surface 366 of the shield that slidably fit in helical grooves 266a and 266b of blade 240. The provision of spring arms 395 facilitates the shield's radial outward expansion to cover blade edges 249a and 249b upon a reduction of counterforce as the helix penetrates a body wall.

Figures 15, 16:
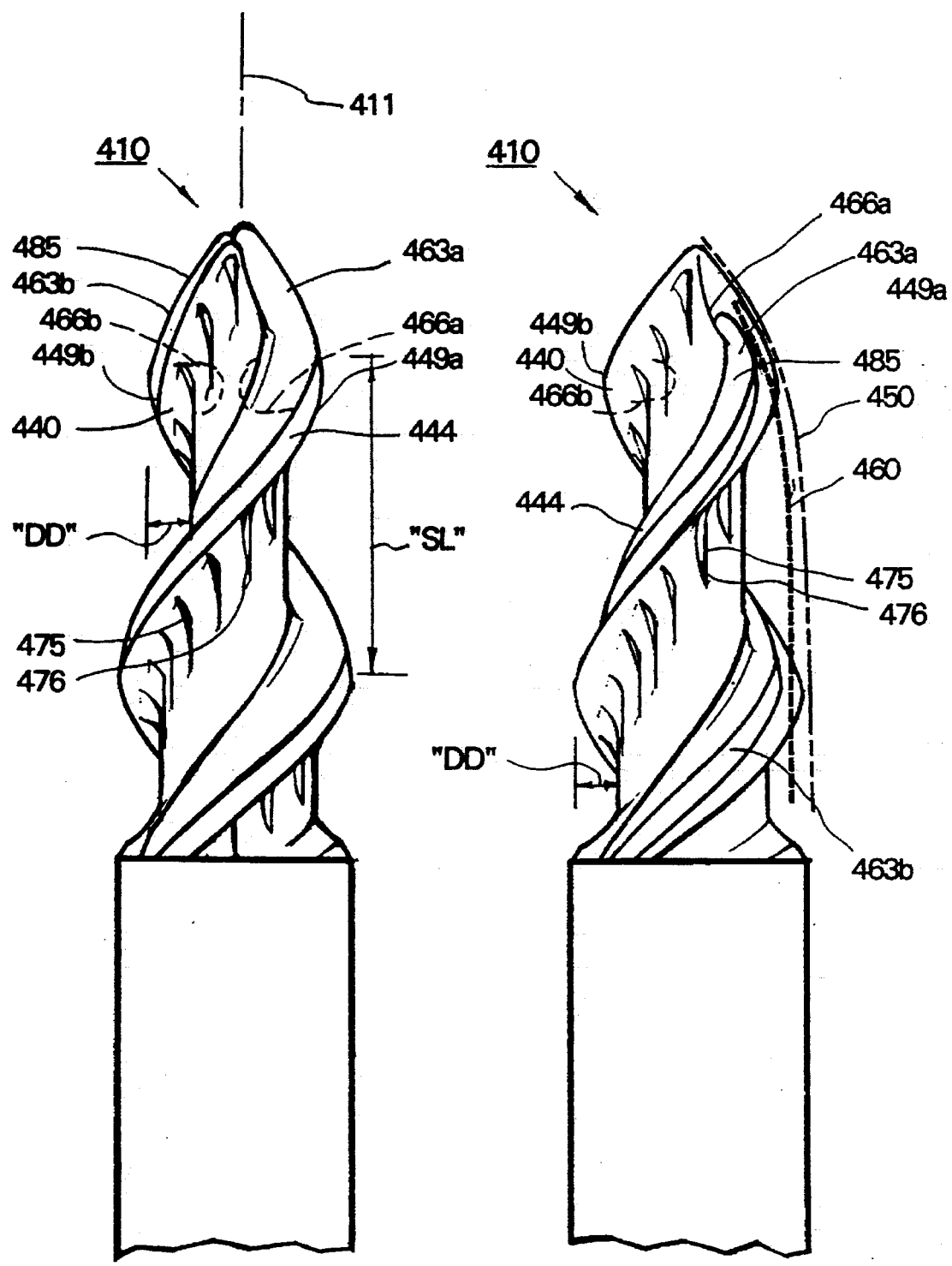
FIG. 15 is an elevational view of a helix subassembly of an alternative embodiment of helical trocar in a non-incising position.
FIG. 16 is an elevational view of the helix subassembly of FIG. 15 in an incising position.

Now referring to FIGS. 15—16, another embodiment of helical trocar that is similar to trocar 205 of FIG. 9, having helix assembly 410 (axis 411) that is suitable for incising a pathway through a body wall. Helix 410 has blade element 440 and shield element 444 that mate along helical interfaces and shield 444 is urged in the distal direction by a spring (not shown) as seen in trocar 205 of FIG. 9. Helix 410 has blade edges 449a and 449b, blade periphery 450 and shield periphery 460. Helix 410 differs from the above-described embodiments in that the shield's protruding portions 463a and 463b are disposed in helical channels 466a and 466b that are distal to blade edges 449a and 449b. Also, the shield's spiral portions 463a and 463b have a thin longitudinal cross-section (less surface area) allowing the spiral portions to spring forward (distally) upon penetration on a body wall with less tissue drag on spiral portions 463a and 463b.

Helix 410 of FIGS. 15–16 also has a greater spiral lead "SL" than above-described embodiments, which also fall within the scope of the present invention as described above. In order to apply proximal traction on a body wall with helical trocar 405, it is necessary to have adequate depth "DD" of helical protrusions to threadably engage tissue. Such proximal traction is facilitated in earlier embodiments by a lesser spiral lead dimension (e.g., 0.750" or less). As shown in FIGS. 15–16, spiral lead "SL" is approximately 1.25". In utilizing a faster spiral lead helix assembly 410 to threadably engage tissue for traction purposes, barb-like notches or gashes 475 are disposed in blade element 440. Gashes 475 have a face 477 that helps prevent blade 440 from counter-rotating when embedded in tissue. It should be appreciated that gashes 475 may be disposed at any suitable angle across helical channel portion 480 of blade 440.

Helix 410 has a non-incising position (FIG. 15) and incising position (FIG. 16) that are similar to above-described embodiments. FIG. 16 shows blade periphery 450 disposed within shield periphery 460, as when tissue counterforce is applied to distal portion 485 of shield 444. The manner of utilizing helical trocar 405 to perform the method of the present invention in incising a pathway through a patient's body wall generally corresponds to above-described FIGS. 7A through 7F. As the surgeon helically advances the distal end of instrument 405 into the body wall, tissue drag causes shield 444 to be counter-rotated (helically and proximally) relative to blade 440 overcoming the force of a spring (not shown). Upon penetration of the body wall, relaxation of tissue drag on distal end 485 of shield 444 causes the shield to move helically and distally under the force exerted by the spring.

Figures 19, 20:
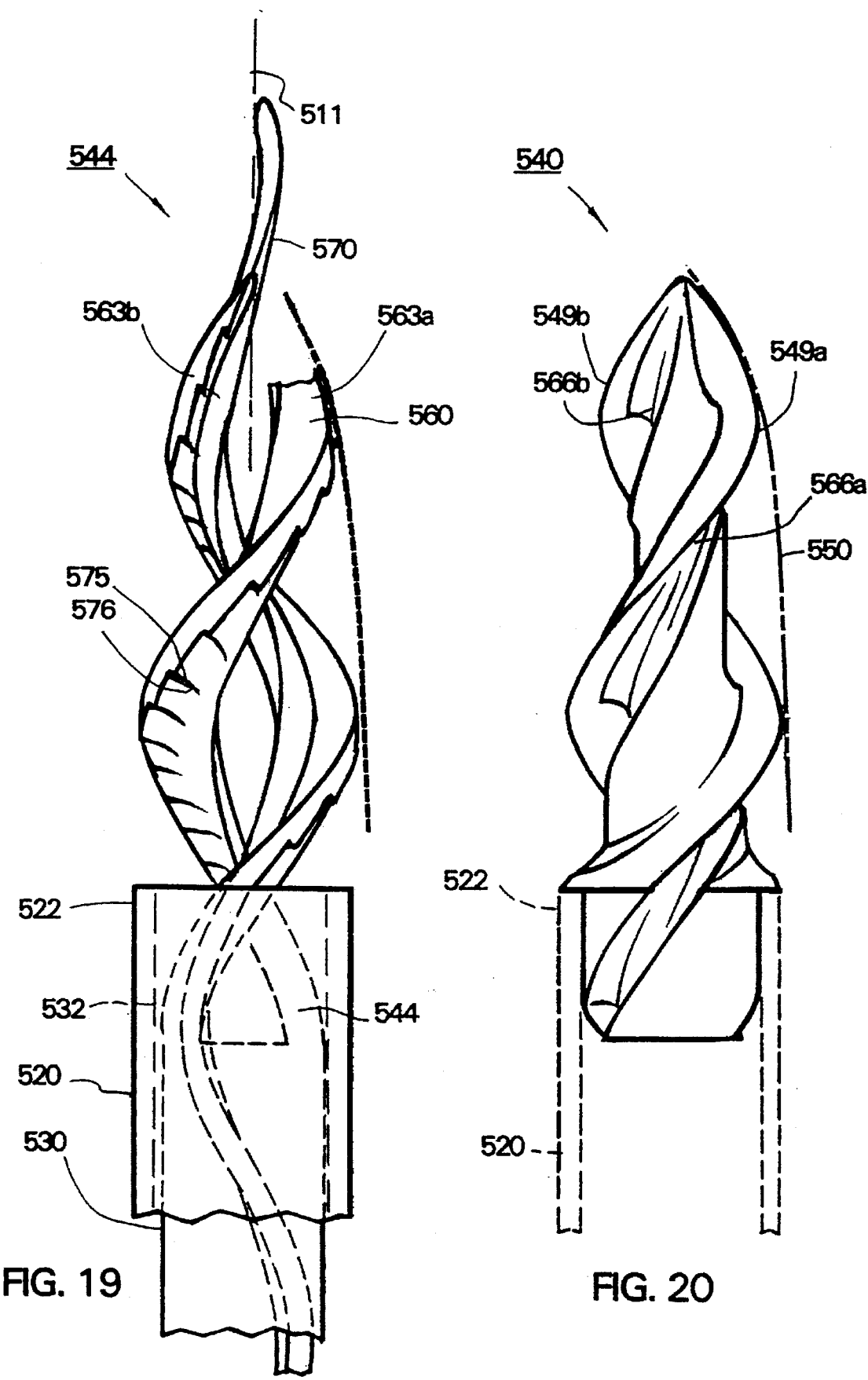
FIG. 19 is an elevational view of a de-mated second element or shield element and probe element of the helix subassembly of FIG. 17.
FIG. 20 is an elevational view of a de-mated first element or blade element of the helix subassembly of FIG. 17.

Now referring to FIGS. 17–20, another embodiment of helical trocar, and more particularly, helix assembly 510 having axis 511 is shown. Introducer sleeve 520 (FIG. 17) having distal end 522 is dimensioned to slide within a standard-sized trocar sleeve. Inner sleeve 530 (FIGS. 17–19) is slidably disposed in axial bore 532 of outer sleeve 520. Inner sleeve 530 is urged in the distal direction by a shield spring (not shown) as in above-described embodiments (see FIG. 9). As can be seen in FIG. 20, blade 540 (shown de-mated) is fixed to distal end 522 of sleeve 520. Similar to above-described embodiments, blade edges 549a and 549b, blade periphery 550 and shield periphery 560 are shown in FIG. 18. Shield 544, is shown de-mated in FIG. 19 having spiral portions, 563a and 563b, and is coupled to inner sleeve 530 (Cf. FIG. 9). Spiral portions, 563a and 563b, are slidably disposed in respective helical channels, 566a and 566b, in blade 540 (see FIG. 20).

Helix 510 differs from the above-described embodiments in that helical probe element 570 is adapted to cooperate with blade 540 and shield 544. As can be seen in FIGS. 17 and 19, probe element 570 is disposed in channel 566a inwardly of spiral portion 563a. Probe element 570 is urged in the distal direction by a separate probe compression spring (not shown) which is similar and concentric to shield spring 235 shown in FIG. 9. Such probe spring may have an equal or greater spring constant than the spring that urges shield 544 in the distal direction.

As shown in FIGS. 17–20, to facilitate threadable engagement with tissue, gashes 575 are disposed in shield element 544. Gashes 575 have a face 576 that to some extent prevents helix subassembly 510 from counter-rotating when embedded in tissue. It should be appreciated that gashes 575 may be disposed at any suitable angle.

The manner of utilizing helical trocar 505 to perform a method of the present invention in incising a pathway through a patient's body wall generally corresponds to above described FIGS. 7A through 7F. As the surgeon presses the distal end of helix assembly 510 into a nick in the patient's skin, probe 570 retracts proximally overcoming the force of the probe spring. As the surgeon further helically advances the instrument, tissue drag on shield 544 (spiral portions 563a and 563b) causes the shield to be counter-rotated (helically and proximally) overcoming the shield spring to expose the sharp blade edged. Upon penetration of the body wall, the relaxation of counterforce on the distal end of the instrument first causes probe 570 to project distally thereby pushing internal organs away from the instrument. Also upon penetration of the body wall, the relaxation of counterforce on the distal end of spiral portions 563a and 563b causes the shield to move helically and distally under the force exerted by the shield spring thus preventing any sharp blade edge from entering into the abdominal cavity.

Although probe 570 is depicted as a helical element slidably disposed in helical channel 566a, a probe also may be a spring-loaded axial-reciprocating element, either on centerline axis 511 or slightly off the centerline of the instrument.

Yet another helix assembly (not shown) may be provided with endoscopic viewing capabilities and fall within the scope of the present invention. For example, an endoscopic viewing helix has a blade element and a shield element that are molded of any suitable transparent plastic (e.g., acrylic plastic) that has a relatively sharp edge. The blade element may have a metal blade insert at its distal tip, for example made of razor blade-type material (0.003" to 0.010" thick stainless steel). The transparent helix assembly has an axial partial bore extending therethrough and adapted to receive a conventional 5 mm. to 8 mm. endoscope.

Although specific embodiments of the present inventions have been described above in detail, it will be understood that this description is merely for purposes of illustration. Specific features of the invention are shown in some drawings and not in others, and this is for convenience only and any feature may be combined with another in accordance with the invention and are intended to fall within the scope of the appended claims.

What is claimed is:

1. An incising assembly for an incising end of a surgical instrument, comprising:

an incising assembly having first and second elements mating along helical interfaces and being at least partly moveable relative to one another along said interfaces, thereby transforming said assembly between an incising position providing at least a distal portion of said assembly in a sharp configuration capable of incising tissues and a non-incising position providing said at least distal portion in a dull configuration not capable of incising tissue; and a spring structure coupled to said incising assembly, thereby urging said assembly toward said non-incising position from said incising position.

2. The incising assembly of claim 1, wherein said second element is in part compressible radially inwardly along said interfaces, thereby to transform said assembly to said incising position from said non-incising position.

3. The incising assembly of claim 1, wherein said incising assembly transforms to said incising position from said non-incising position in response to a counterforce being applied to a distal portion of said second element.

4. The incising assembly of claim 3, wherein said counterforce is at least partly axial.

5. The incising assembly of claim 3, wherein said counterforce is at least partly rotational.

6. The incising assembly of claim 3, wherein said counterforce is caused by anatomic tissue.

7. The incising assembly of claim 1, wherein said spring structure is of a resilient material and is a portion of said second element.

8. The incising assembly of claim 1, wherein said spring structure is a spring urging said second element distally and helically.

9. The incising assembly of claim 1, wherein said second element is of resilient material having a first outer periphery in a response state and having a second outer periphery in a suspense state, said second outer periphery being at least partly radially inward of said first outer periphery in said incising position.

10. The incising assembly of claim 1, wherein said second element is of resilient material having a first outer periphery in a repose state and having a second outer periphery in a suspense state, a proximal portion of said second outer periphery being radially inward of said first periphery and a distal portion of said second outer periphery being radially outward of said first outer periphery in said incising position.

11. The incising assembly of claim 1, wherein said second element is of resilient material having a first outer periphery in a repose state and having a second outer periphery in a suspense state, said second outer periphery being radially outward of a periphery of said first element in said non-incising position.

12. The incising assembly of claim 1, wherein said first element is at least partly of transparent material.

13. The incising assembly of claim 1, wherein said second element is at least partly of transparent material.

14. The instrument of claim 1, further including a cannula removably mounted around said instrument.

15. An incising assembly for an incising end of a trocar-type instrument, comprising:

an incising assembly comprising first and second elements mating along helical interfaces and defining a helically-protruding edge for threadably engaging an anatomic structure and movable relative to one another along said interfaces, thereby transforming said assembly between an incising position and a non-incising position, said incising position providing at least a distal portion of said edge in a sharp configuration capable of incising tissue, said non-incising position providing said at least distal portion of said edge in a dull configuration not capable of incising tissue;

a spring structure urging said assembly toward said non-incising position from said incising position;

a probe element with a distal tip and mating along said helical interfaces of said first and second elements and moveable between a projected position and a retracted position, in said projected position said distal tip being distal of distal ends of said first and second elements, in said retracted position said distal tip being proximal of said distal ends of said first and second elements; and a probe spring coupled to said probe element, thereby urging said probe element toward said projected position from said retracted position.

\* \* \* \* \*